United States Patent [19]

Schumacher et al.

[11] Patent Number: 5,248,393
[45] Date of Patent: Sep. 28, 1993

[54] SOLVENT REPROCESSING SYSTEM

[75] Inventors: J. Randolph Schumacher, North Caldwell, N.J.; Gregory E. Carr, Portland, Oreg.; Martin J. Striefler, Middlesex, N.J.

[73] Assignee: S&K Products International, Inc., Chestnut Ridge, N.Y.

[21] Appl. No.: 473,169

[22] Filed: Jan. 31, 1990

[51] Int. Cl.⁵ .......................... B01D 3/32; B01D 3/42
[52] U.S. Cl. ...................................... 202/158; 34/74;
68/18 C; 68/18 F; 68/18 R; 68/19; 202/164;
202/168; 202/170; 202/181; 202/185.5;
202/202; 202/206; 202/200; 203/1; 203/95;
203/96; 203/100; 203/DIG. 18; 210/323.1;
210/806
[58] Field of Search ............... 202/170, 158, 206, 181,
202/164, 168, 185.5, 202, 200; 34/74;
210/323.1, 806; 68/18 F, 18 C, 18 R, 19; 203/1,
DIG. 18, 95, 96, 100

[56] References Cited

U.S. PATENT DOCUMENTS

| | | | |
|---|---|---|---|
| 4,012,847 | 3/1977 | Rand | 68/18 F |
| 4,241,034 | 12/1980 | Kolich | 423/300 |
| 4,513,590 | 4/1985 | Fine | 68/18 F |
| 4,601,181 | 7/1986 | Privat | 68/18 F |
| 4,712,392 | 12/1987 | Aagiwara et al. | 202/170 |
| 4,765,159 | 8/1988 | Maeda et al. | 68/18 F |
| 4,781,041 | 11/1988 | Fowler | 68/18 F |
| 4,830,710 | 5/1989 | Thompson | 202/170 |
| 4,885,099 | 12/1989 | Kelly | 203/95 |
| 4,909,050 | 3/1990 | Sewter et al. | 68/18 F |

Primary Examiner—Virginia Manoharan
Attorney, Agent, or Firm—Hugh D. Jaeger

[57] ABSTRACT

A compact solvent reprocessing system for use in a limited physical area. Solvents to be reprocessed is contacted by deionized water in a water wash column and delivered to a distillation column where waste solvent is separated from materials that boil at a higher temperature than the waste solvent. Distilled solvent is delivered to a drying column and final filters for removal of any other foreign materials. The modular solvent reprocessing system to reclaim/recycle high purity solvents on-site at a manufacturing facility. A system includes a pumpless pressurized tank solvent transfer units, storage tanks, liquid-liquid extraction column, distillation columns, submicron filtration units, and water and acid adsorption columns arranged as necessary to produce ultra-high purity solvents from waste solvent streams. The systems are packaged in modular assemblies with secondary containment to meet U.S. EPA requirements.

21 Claims, 7 Drawing Sheets

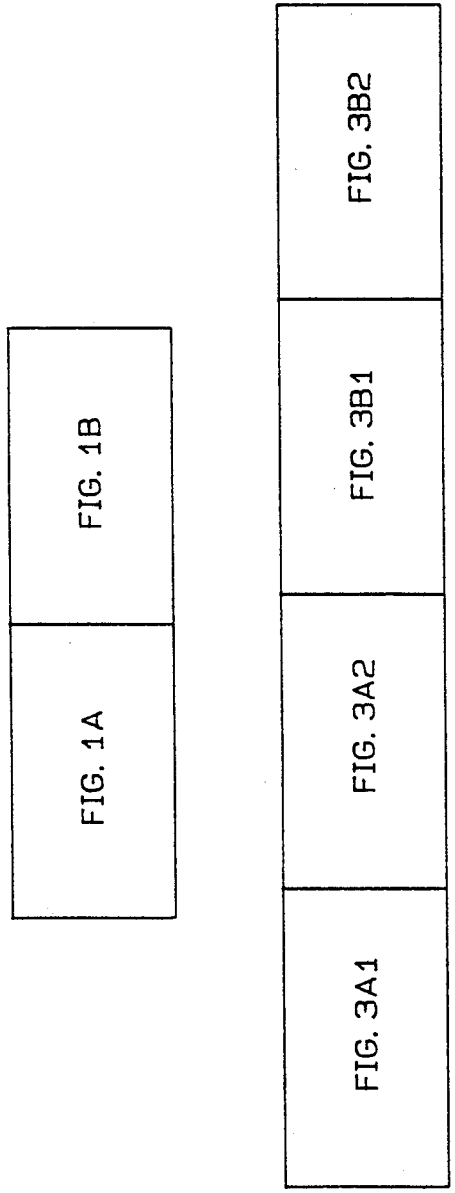

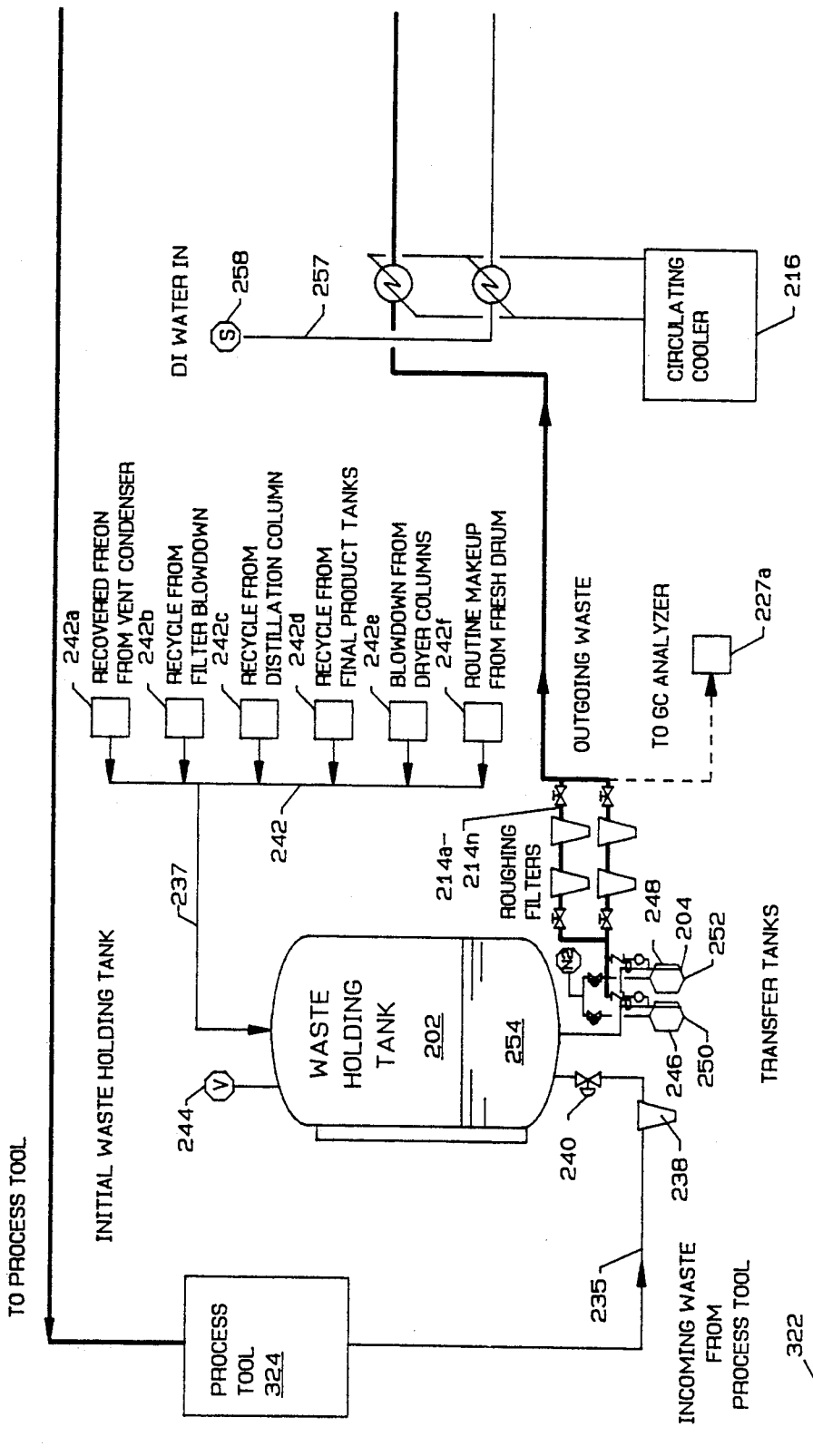
FIG. 3A1

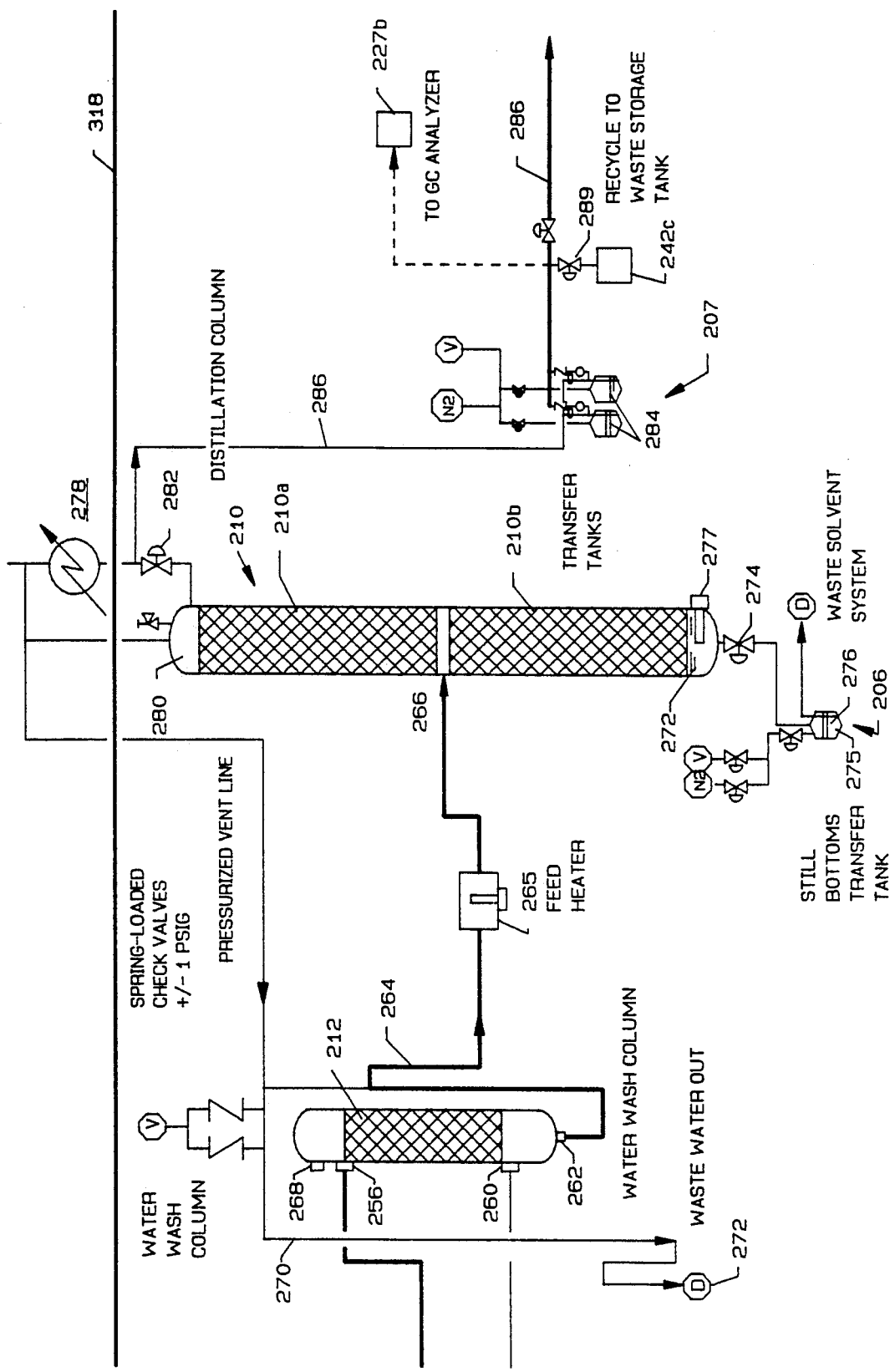
FIG. 3A2

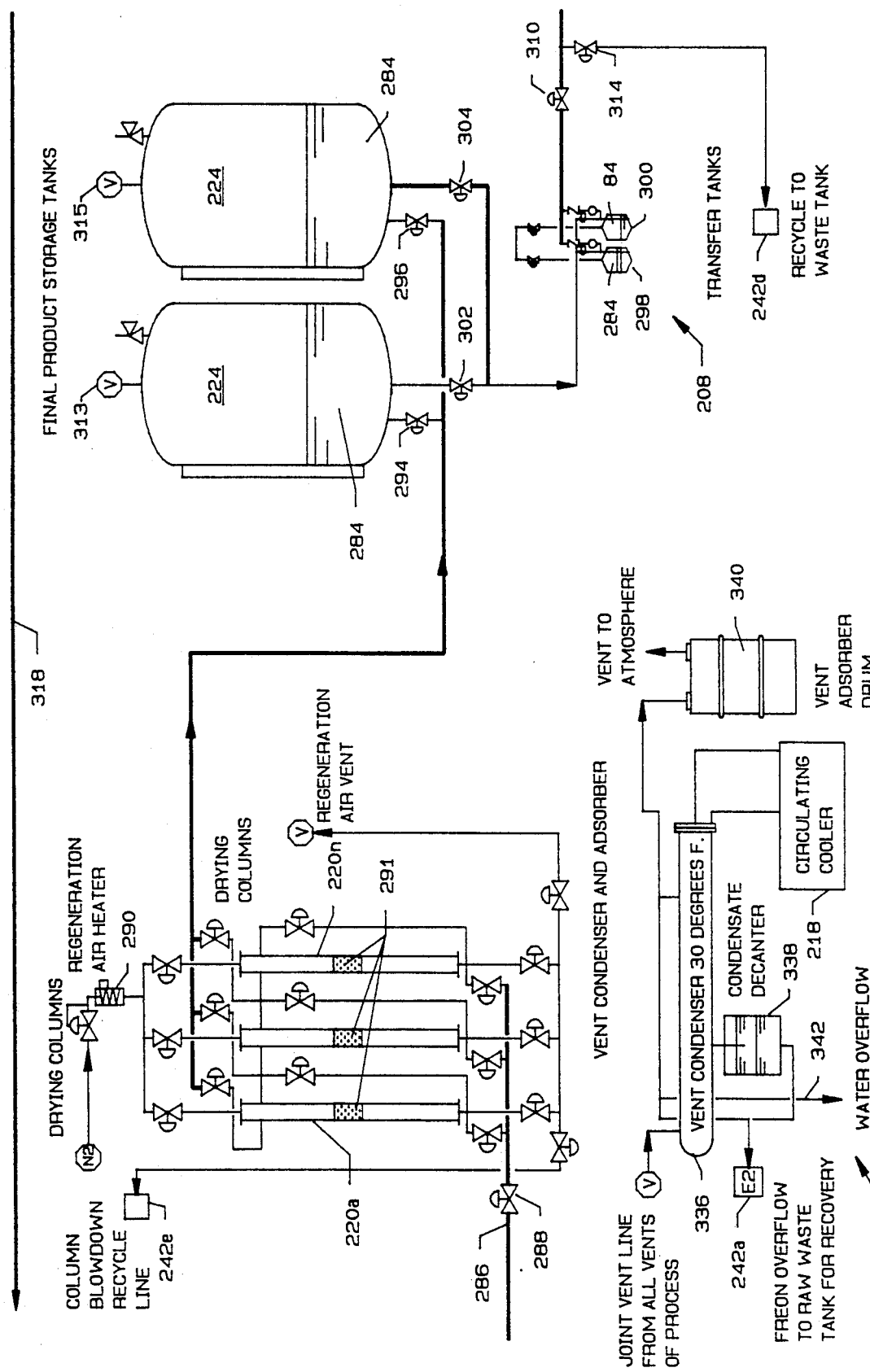
FIG. 3B1

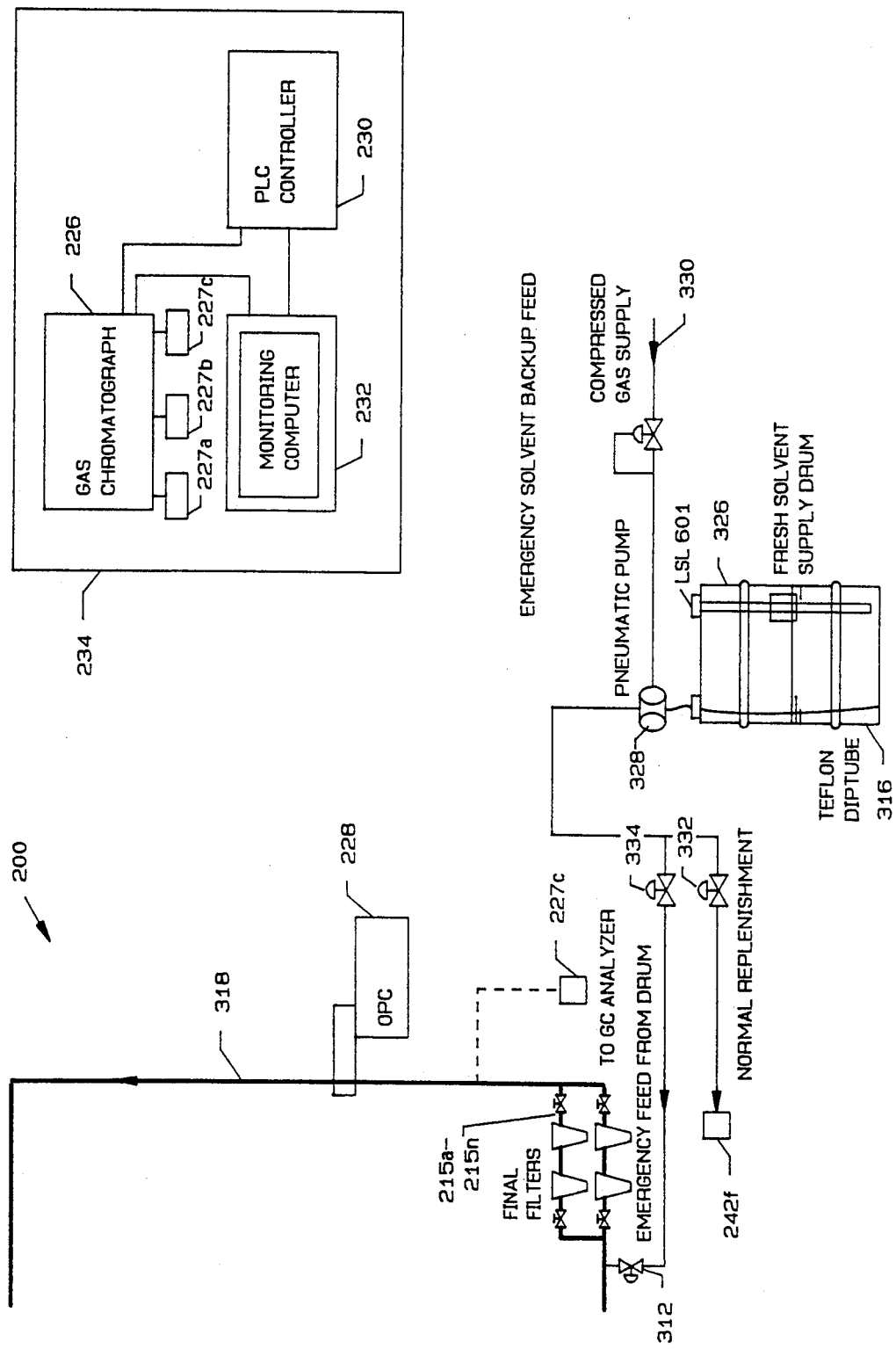
FIG. 3B2

SOLVENT REPROCESSING SYSTEM

BACKGROUND OF THE INVENTION

1. Field of the Invention

The present invention is for a solvent reprocessing system, and more particularly, pertains to a solvent reprocessing system for a variety of solvents to high purity levels.

2. Description of the Prior Art

Existing on-site solvent reclamation/recycling units offer only single-stage distillation without submicron filtration or solvent drying capabilities. More complex systems are not offered in modular construction with integral secondary containment. No existing systems are designed specifically to reprocess solvents to SEMI specifications or higher quality standards.

The present invention provides a solvent reprocessing system which processes a solvent to a high purity level at an inhouse location.

SUMMARY OF THE INVENTION

The general purpose of the present invention is an on-site solvent reprocessing system that reprocesses a variety of solvents to purity levels, even to a degree higher than SEMI specifications. The system can be operated in batch or continuous mode with any desired degree of automation and handles a wide variety of waste solvents of differing purity levels. The system can also include continuous on-line analysis for impurities, water, particulates and acidity; explosion-proof construction for handling flammable solvents; inherent flexibility to allow modification in case of solvent changes; continuous PC-based data acquisition and control system; and manual semi-automatic or completely automatic operation. The components of the reprocessing system are arranged in preassembled modules with integral secondary containment of all fluid-processing modules. All system operations are designed to minimize vapor and liquid losses, controlling toxic or environmentally hazardous materials. The exact system configuration depends on the solvent being processed, the contaminants in the solvent and the desired purity of the finished product.

One significant aspect and feature of the present invention is that in November, 1989, Congress passed a new Excise Tax effective January, 1990, on the use of Freon and other ozone depleting chemicals. An inhouse processing system will be completely tax exempt.

Another significant aspects and features of the on-site processing system offers many other benefits to a microelectronics company and the industry in general, including: reduction of hazardous waste volume leaving the plant site; a reliable supply of solvent that is not dependent on outside suppliers; a product quality equal to or better than existing purchased product; reduction of waste disposal cost and potential environmental liability; reduction of purchased material cost; fulfills the requirements of EPA and State waste minimization regulations; does not require a Part "B" RCRA permit; completely enclosed systems minimize operator exposure to solvents; automatic still bottoms transfer and handling; and depending upon the contaminants in the waste, yields can be as high as 95% to 99.99% based on the feed solvent.

Other significant aspects and features include modular design with integral secondary containment of fluid processing units; integrated liquid/liquid extraction and distillation column for simplified operation; pumpless liquid transfer via pressurized tanks with solvent filling and emptying tank through one nozzle with dip pipe minimizes particulate generation. The design is optimized for production of high-purity solvent at a relatively low processing through-put. It offers unprecedented safety of operation and containment of liquids being processed.

Further significant aspects and features of the reprocessing system include integrated water/solvent extraction column and distillation column simplifies process; pumpless material transfer via pressurized tanks with only two connectors to minimize particulate contamination; significantly higher product quality than other on-site units to accept micro-electronic specifications; and integral secondary containment of fluid processing modules to eliminate external leaks in case of spills.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 5 1A and 1B illustrates a plan view of a solvent reprocessing system, the present invention;

FIG. 2 illustrates the alignment of FIGS. 1A and 1B and FIGS. 3A1-3A2 and 3B1-3B2; and, FIGS. 3A1-3A2 and 3B1-3B2 illustrate an alternative embodiment of a solvent reprocessing system.

DESCRIPTION OF THE PREFERRED EMBODIMENT

Figure 1A:
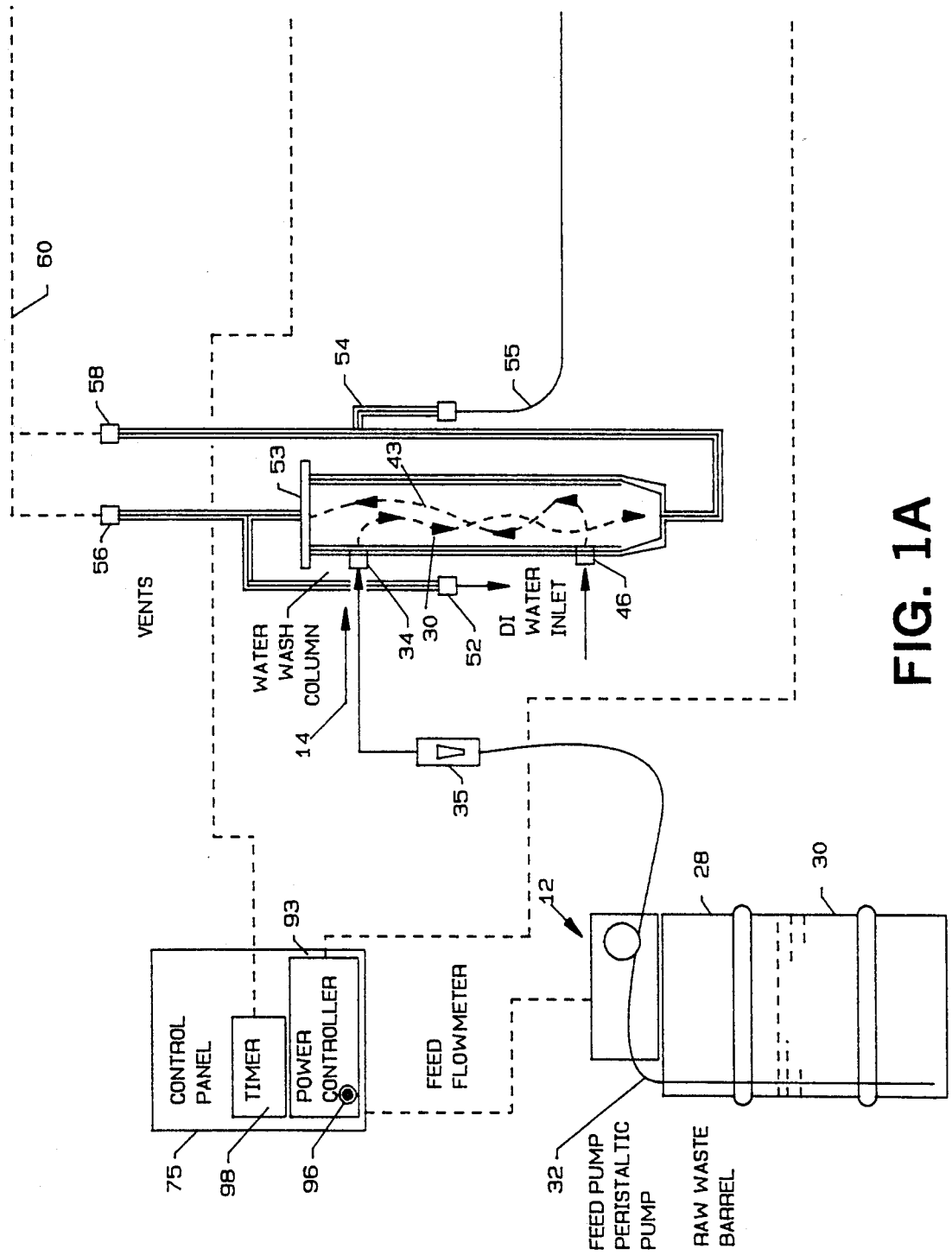
Figure 1B:
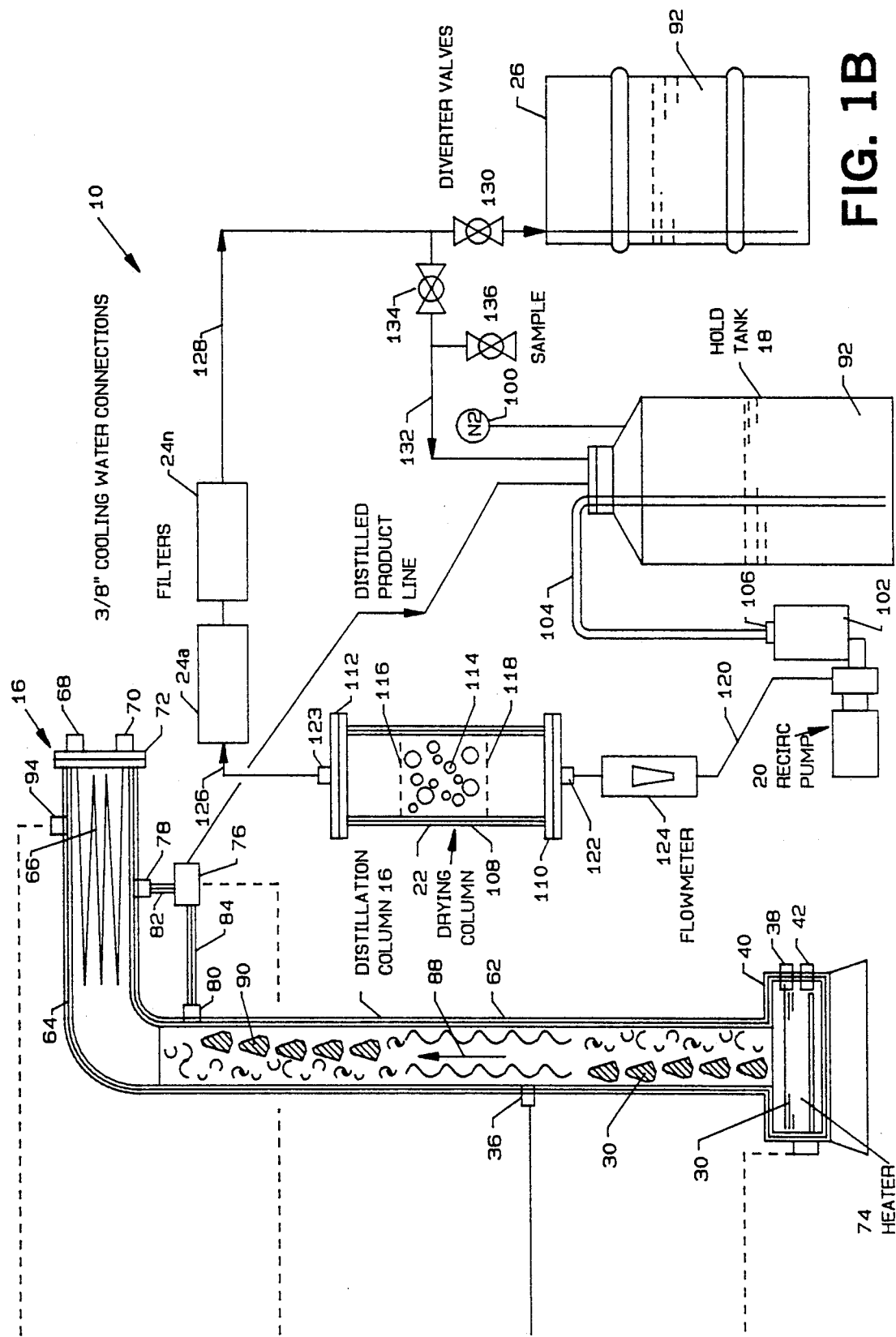

FIGS. 1A-1B illustrates a compact solvent reprocessing system 10 for use in a small or confined area. The system incorporates a number of main components including, but not limited to, an initial feed pump 12, a water wash column 14, a distillation column 16, a hold tank 18, a product circulation pump 20, a plurality of dryer columns including dryer column 22, a plurality of filters including filters 24a-24n and a product tank 26.

The initial feed pump 12 is a peristaltic type feed pump which operates by having a rotating rotor that squeezes a flexible Viton tubing inside a fixed housing. This type of pump is used because it can self-prime, and thus can pull fluid out of the initial waste tank 28 of incoming waste solvent 30. One end of the tubing 32 is inserted into the initial waste tank 28 and the other end is attached to the wash column inlet 34 of the water wash column 14 through a feed flow meter 35 as illustrated, or in the alternative to the distillation inlet 36 of the distillation column 16 as desired. The initial feed pump 12 is actuated by a high lever switch 38 and a low level switch 42 in the bottom chamber 40 of the distillation column 16. When the liquid level is low, the initial feed pump 12 is actuated by a low position of level switch 38 and the initial feed pump 12 turns on. This will refill the bottom chamber 40 until the liquid level in the bottom chamber 40 rises again. There is approximately ½" of deadband in the level switches.

The water wash column 14 is used to contact the incoming waste solvent 30 with a supply of deionized water to remove water-soluble compounds. The deionized water 43 enters the lower portion of the water wash column 14 through port 46. Unprocessed waste solvent 30 is fed into a washing column inlet 34 at the top of the water wash column 14. The deionized water 43 is forced out of the top of the water wash column 14. Since waste solvent 30 will not mix with deionized water 43, and is heavier than water, the waste solvent 30 will fall down through the upflowing deionized water stream 43 and collect at the bottom of the water wash column 14. Both the waste solvent 30 and the deionized water 43 will overflow out of the water wash column 14, through different ports. The deionized water 43 flows out of a top piped port 52 to a drain, and the waste solvent 30 flows through a piped port 54 located below the level of the piped port 52. Vents 56 and 58 are connected from the piped port 52 extending from the top of flanged plate 53 and from the piped port 54. Waste solvent 30 flows by gravity from the bottom of the water wash column 14, through the piped port 54, and through a hose 55 into distillation inlet 36 on the mid portion of the distillation column 16.

The distillation column 16 is used to separate the waste solvent 30 from materials that boil at a temperature higher than the waste solvent 30. The distillation column 16 has several components, including a stainless steel bottom chamber 40, a tower section 62 filled with packing, a condenser section 64 with internal cooling coil 66, a cooling coil inlet 68, and a cooling coil outlet 70 at the condenser section plate assembly 72. A low flux electric heater 74 with a chemically resistant element and level switches 38 and 42 are housed in the bottom chamber 40. The low level switch 42 also turns off the heater 74 at a low solvent level in the bottom chamber 40. The high level switch 38 turns initial feed pump 12 on and off to maintain the bottom chamber 40 level. A control panel 75 controls the initial feed pump 32, heater 74 and a reflux solenoid valve 76. The three-way reflux solenoid valve 76 is located under condenser section 64 between a port 78 on the condenser section 64 and a port 80 on the tower section 62. Pipes 82 and 84 plumb the reflux solenoid valve 76 to ports 78 and 80. Another flexible pipe 86 connects the three-way solenoid 76 to the holding tank 18. The distillation column 16 works by boiling the waste solvent 30 in the bottom chamber 40 with the electric heater 74. The solvent vapors 88 rise through the distillation column 16, meeting a stream of down falling liquid reflux 90 along the way. The solvent vapors 88 are condensed in the condenser section 64. Some of the condensed liquid, known as reflux 90, is returned to the distillation column 16 to provide the down falling liquid. The rest of the liquid coming out of the condenser and through the reflux solenoid valve 76 is the final liquid distillate 92, which is deposited through the flex pipe 86 into the holding tank 18. The electric heater 74 is controlled by a power controller 93. This power controller 93 regulates the amount of heat coming out of the electric heater 74, which in turn determines the amount of material being boiled. It may be necessary to regulate the "boilup" to keep from overloading the condenser section 64. Too much boilup is evident by a loss of vapor through a top vent 94 of the distillation column 16, or too much column pressure. The electric heater, 74 also has a safety relay in the power controller 93 to cut off power in case of low liquid level in the bottom chamber 40. To start the electric heater 74, there must be sufficient liquid in the bottom to close low level switch 42. Pushing the heater start button 96 will latch in a relay that energizes the power controller 93. If the liquid level of the waste solvent 30 falls below the safety level, the relay will unlatch and disconnect the power controller 93. The power controller 93 must be manually restarted after a safety shutdown. The reflux solenoid valve 76 is a chemically inert three-way valve located immediately under the water wash column 14. It is controlled by a timer in the control panel 75. The timer is a cycling "on-off" timer. The on and off cycles can be controlled independently The holding tank 18 receives the liquid distillate 92 from the reflux solenoid valve 76 and the flexible pipe 86. The holding tank 18 is held under a slight positive pressure with dry nitrogen 100 to keep out water and dirt. It is made out of cross-linked polyethylene, which is completely compatible with solvents. The circulation pump 20 is a seal-less magnetic drive pump. It has a self-priming chamber 102 on it, allowing the suction line 104 to come out of the top of the holding tank 18 instead of requiring a tap through the bottom or side. The self-priming chamber 102 is filled with solvent and then tightly capped. As the circulation pump 20 draws out the liquid, it creates a partial vacuum that siphons solvent out of the holding tank 18 into the pump inlet 106.

The dryer column 22 is a 316L stainless steel pipe 108 with opposing end flanges 110 and 112. The end flanges 110 and 112 are drilled and tapped to accept $\frac{1}{8}''$ NPT tubing adapters. Inside the column there is about 5 pounds of molecular sieve 114, a ceramic-type pellet material. The molecular sieve 114 is held in place by internal screens 116 and 118 held in between flanges. The sieve 114 as delivered is dry, and can absorb about 15% of its weight in water before it becomes useless. It can be regenerated with hot, dry air, nitrogen or other inert gas. Output of the circulation pump 20 is delivered through a tube 120 to a tubing adapter port 122 on the bottom side of the end flange 110. A flow meter 124 is in series with the tube 120 to indicate flow into the dryer column 22. After drying in the dryer column 22, the dried liquid distillate from adapter port 123 is delivered through tube 126 to the final filters 24a–24n. The filters 24a–24n are a very important part of the solvent reprocessing system 10. They take out the particulate material found in the solvent stream. Most of this particulate material comes from the molecular sieve pellets. The distillation column has taken most of the particulate material out of the feed stream. However, the molecular sieve 114 does shed some material, especially when new. Most of the metallic and elemental contamination in the final product will begin the form of particulate matter. Iron, sodium and other metals are not soluble in solvent and can be removed by filters. Hence the efficiency of the filters will determine the quality of the final product metallic contamination and non-volatile residue as will as particulate levels. Filtered liquid distillate 92 passes from the filters 24a–24n through a tube 128 and a diverter valve 130 into the product tank 26. Another tube 132, with a diverter valve 134 in series, extends between the tube 128 and the holding tank 18. A sample valve 136 extends from the tube 132.

FIG. 2 illustrates the alignment of FIGS. 1A and 1B and FIGS. 3A1–3A2 and 3B1–3B2.

FIGS. 3A1–3A2 and 3B1–3B2 together illustrate an alternative embodiment of a solvent reprocessing system 200.

All wetted equipment is 316L stainless steel, electropolished or passivated to minimize metal contamination of solvent, Teflon or other inert plastics. The system includes a number of components including, but not limited to, a 500-gallon initial waste tank 202; non-maintenance inert gas padded tank transfer systems 204, 206, 207 and 208; 10-foot high, 8-inch distillation column 210 with high-efficiency woven 316L stainless steel internal packing to provide a minimum of 16 theoretical plate separation efficiency; a 4-inch liquid-liquid continuous extractor column 212, also known as a water wash column for removal of water-soluble contaminants; a plurality of dual duplex filters, including filters 214a-214n and 215a-215n, to assure continuous flow during filter changes; circulating chillers 216 and 218 to properly cool and heat product and vents; and a plurality of drying columns including drying columns 220a-220n with internal 4A molecular sieves for removal of water and small organic compounds where regeneration is accomplished automatically without opening the system so that a continuous operation may be provided without introducing external contamination. Also included are a plurality of final product holding tanks including final product holding tanks 222 and 224, a gas chromatograph 226 and optical particle counter 228. A control system is based on a PLC controller 230 with a personal computer 232 running a software package for process monitoring, alarming and control. Controls are mounted in a purged control cabinet 234 for operation in a class 1, division 1 atmosphere. All control valves are remotely operated by pneumatics from solenoids in the purged control cabinet 234. All field electronics have intrinsically safe barriers for safety considerations. Stainless steel or flame-retardant polypropylene enclosures are incorporated, and all enclosures have internal drain pans to completely contain any internal spills of solvents within. The solvent reprocessing system 200 is designed to reprocess solvents 113, such as Freon or others as described herein. Due to the explosion-proof design, versatile distillation column 210 and large drying capacity, the solvent reprocessing system 200 can be modified to purify other solvents of differing flammability, boiling temperatures or contaminants.

A feed stream containing solvent from a process tool and solvent vent return lines and other contaminants is delivered to the initial waste holding tank 202 through lines 235 and 237. Incoming solvent waste from a process tool enters the initial waste tank through a line 235, a filter 238 and a valve 240. Solvent recycle returns are manifolded to a manifold tube 242 and pumped to the top of the initial waste tank 202 through line 237. Solvent recycle inputs to the manifold tube ports 242a-242f. Manifold tube port 242a receives recovered solvent from the vent condenser and absorber 320, manifold tube port 242b receives solvent from filter blow down, manifold tube port 242c receives solvent from the distillation column 210, manifold tube port 242d receives solvent from the final product tanks 222 and 224, manifold tube port 242e receives solvent from dryer column 220a-220n blowdown and the manifold port 242f receives solvent from the emergency solvent backup system 316. A vent 244 is provided at the top of initial waste tank 202. Waste from the initial waste holding tank 202 drains by gravity to one of two pressurized transfer tanks 246 or 248 in the tank transfer system 204. When one of the tanks, such as tank 246, is 90% full, it sends a signal to the PLC controller 230 via an internal magnetic float switch 250. The inlet valve in the tank transfer system 204 is closed, and the transfer tank 246 is pressurized and is placed in a "ready" mode. When the other tank 248 is 15% full, again, sensed by a magnetic float switch 252, the outlet valves in the tank transfer system 204 are switched and the full tank, i.e., transfer tank 246, begins delivering waste solvent product. The filling and emptying ar done by an extended dip tube (not illustrated), minimizing fluid velocity. The only moving parts are the magnetic float switches and the control valves. This lack of moving parts minimizes maintenance, turbulence and particle-generating processes.

The outgoing waste solvent 254 from the tank transfer system 204 is pipe fed through the filters 214a-214n and to a top port 256 at the upper end of the water wash column 212 where it is contacted with deionized water 258 which is inputted through line 257 to a lower port 260 in the water wash column 212 to extract the water-soluble contaminants in the same fashion as described in FIG. 1. The waste solvent 254 and deionized water 258 are cooled by circulating chiller 216 before entering the column to 45° F. to minimize the solubility of water in the solvent. The waste solvent 254 then leaves the bottom of the water wash column 212 through a bottom port 262, a pipe 264 and a feed heater 265 and flows by gravity directly into the distillation column 210. The deionized water 258, having just scrubbed the waste solvent 254, flows out the top port 268 of the water wash column 212 and flows by gravity through a pressurized drain pipe 272 or pump station.

The washed waste solvent 254 enters the distillation column 210 in the side feed port 266. This feed location provides for an upper stripping section 210a to provide a good quality product, and a lower enriching section 210b to boil most of the waste solvent out of the still bottoms 272. The still bottoms 272 are drained out at regular intervals through a drain valve 274 as governed by its temperature. The boiling temperature of the bottoms 272 is a sensitive indicator of the dissolved contaminants in the liquid. These bottoms are drained by gravity into a single vented pneumatic transfer tank 275 through the drain valve 274. It is then pressurized by nitrogen and the waste solvent 276 blown into an effluent solvent system or waste container as desired such as a 55 gallon waste container. The distillation column 210 is packed by 7 feet of high-efficiency woven mesh packing. It has an electric heating coil 277 in the still bottoms 272 for heat and a horizontal condenser 278 for cooling the tops 280. Some of the condensed tops fluid are returned to the distillation column 210 as reflux through an external 3-way solenoid valve 282. The remainder is sent on as distilled solvent product 284 and is routed by a connected line 286 through the transfer tank system 207 which operates much the same as the transfer tank system 204. From the transfer tank system 207, the distilled solvent product 284 is sampled by a gas chromatograph 226 at 227b and is also sent through line 286 and a valve 288 to the drying columns 220a-220n. Another valve 289 is provided in line 286 for recycling of distilled solvent product at a point 242c back to the initial waste tank 202 through manifold 242. The end of the still bottoms 272 can be removed for cleaning or inspection.

The distilled solvent product 284 is dried by passing it through molecular sieve material in the drying columns 220a-220n. The molecular sieve 291 has a pore size of 4 angstroms, which will remove water and small organic compounds such as alcohols. There are three drying columns, including columns 220a-220n, operated in a round robin fashion. Two columns are treating the product in a lead-lag configuration while the third column is being regenerated. At an appropriate schedule, the columns are switched, with the lag column becoming the lead, the regenerated column becoming the lag and the lead column isolated to be regenerated. This process assures the best column performance and lowest product contamination levels at a constant product flow. No operator attention is needed for the entire operation. The columns 220a-220n are regenerated by blowing hot, dry nitrogen or other inert gas through them. The gas is heated by an in-line electric heater 290. A regeneration temperature of 250° F. is sufficient to assure good regeneration. The temperature of the regeneration air and the exhausted air are monitored to determine the end of the regeneration cycle. A series of automatically operated valves at the upper, lower and midsection allow for accomplishment of regeneration of the sieve material therein. The regeneration air heater 290 is plumbed to the top side of the drying columns 220a-220n. The distilled solvent product 284 then passes through a line 292, through valves 294 and 296, and into vented tanks 222 and 224. Distilled solvent product 284 is delivered to the tank transfer system 208 and tanks 298 and 300 via valves 302 and 304 in the drain line system 306. The distilled solvent product 284 is filtered through the final dual duplex filters 215a-215n. The two-stage filtration through submicron filters removes the particulate contamination. Two sets of filters allows product flow while changing the filters without bypassing. Blowdown valves allow the recovery of the solvent contained in the filter housings back to the initial waste holding tank through manifold port 242b, minimizing produce loss. A line 308 plumbs the transfer tanks 298 and 300 to the final filters 215a-215n from transfer tank system 208 and includes a valve 310. Valves 312 and 314 tee off of line 308 for recycling of distilled solvent product 284 to the initial waste tank 202 through manifold port 242d and for connection to the emergency solvent backup system 316. The final product holding tanks include vents 313 and 315.

The gas chromatograph 226 is used to monitor the incoming waste at 227a, the distillation column product at 227b and the output of the final filters 215a-215n at 227c to assure the proper operation of the solvent reprocessing system 200. The particles in the finished product are monitored by an optical particle counter 228. Both the gas chromatograph 226 and the optical particle counter 228 are tied into the PLC controller 230 via alarm contacts to initiate automatic process corrections including automatic shutdown. After passing through the optical particle counter 228, the filtered distilled product 284 passes through line 318 to be used by a process tool 324. The solvent reprocessing system 200 includes an automatic backup where uninterrupted flow is guaranteed. The system feeds virgin solvent in two ways. To make up for vapor losses, the virgin solvent is fed into the initial waste holding tank 202 to maintain level. This way, the virgin solvent will receive the same purification as the distilled solvent product 284, assuring the same product quality. In case of a system shutdown, the virgin solvent from the emergency solvent backup system 316 is fed directly into the product line to continue product flow to the process tool. The solvent reprocessing system 200 also includes a vent condenser and absorber system 320. Nitrogen pressurization, drains, and atmospheric vents and other connections are indicated throughout in FIGS. 3A-3B by appropriate symbols as depicted in the key 322.

The emergency solvent backup system 316 includes a fresh solvent supply drum 326 connected to a pneumatic pump 328 powered by a compressed gas source 330. Output of the pump 328 is directed through a valve 332, through port 242f of manifold 242 and into the waste holding tank to deliver routine makeup solvent fluid. Fresh solvent fluid is also delivered through valve 334 and valve 312 to line between the tank transfer system 208 and the plurality of final filters 215a-215n as emergency feed from the fresh solvent supply drum 326.

The vent condenser and absorber system 320 includes a vent condenser 336 which receives vapors from various system vents which are condensate, collected in a condensate decanter 338 and returned to the waste holding tank 202 through port 242a. Circulating chiller 218 provides for cooling of the vent condenser 336. A vent absorber drum 340 also connects to the vent condenser 336. Waste water is drained overboard through line 342.

MODE OF OPERATION

Appropriate solvents for reprocessing are:

Chlorinated Solvents

Tricholoroethylene (TCE)
1,1,1, Trichloroethane (TCA)
Methylene Chloride
Perchloroethylene Trichlorotrifluoroethane and Related Azeotropes Freon TF,TA,TE,TES.TMC,TMS
Diaflon 23,23-MC,23-3,S3-ES
Genesolv etc.

Alcohols (not water saturated)

Methyl Alcohol
Ethyl Alcohol
Isopropyl Alcohol
Butyl Alcohol

Ketones

Methyl Ethylketone (MED)
Methyl Isobutylketone (MLBK)

Aromatics

Xylene

Other solvents such as n-methyl pyrrolidane and acetone may be possible to recycle depending upon impurities.

The previous discussion of FIGS. and 3 also describe the mode of operation.

Various modifications can be made to the present invention without departing from the apparent scope hereof.

We claim:

1. A solvent reprocessing system comprising: a waste tank for storing waste solvent; a first flow meter; a feed pump connected for fluid flow to said first flow meter and to an upper portion of a water wash column; first pipe means connected to the upper portion of said water wash column; second pipe means connected to the bottom of said water wash column; vent means connected to said first pipe means and to a condenser system of a distillation column, said second pipe means at the bottom of said water wash column connected to a midsection of the distillation column, said distillation column including an upper section, a bottom chamber and said condenser system, a heater in said distillation bottom chamber for heating solvent including a low level switch and a high level switch; said condenser system including an internal cooling coil; and means for connecting cooling water to said cooling coil, and reflux solenoid valve, means for connecting said reflux solenoid valve between said condenser system and said upper section of the distillation column; control means including a timer, a power controller and means for connecting to said timer the power controller and means for connecting said controller to said feed pump and to said heater, a hold-tank, said reflux solenoid valve connected through a flexible pipe to said hold tank; a circulation pump; a suction line connected between said hold tank and said circulation pump; a second flow meter; a drying column, said second flow meter connected between said circulation pump and said drying column; a plurality of filters, said drying column connected to said plurality of filters; a product tank, said plurality of filters connected to said product tank, and a valving system connected between said product tank and said hold tank.

2. A solvent reprocessing system comprising a waste holding tank including means for receiving and storing solvent and connected to a first transfer tank system, said first transfer tank system connected to a plurality of first filters, said filters being connected to a first top port of a water wash column, the water wash column having a lower port located at a lower portion of said water wash column for deionized water input, a circulating chiller connected across said first top port and said lower port of said water wash column, a second top port of said water wash column being connected to a drain pipe, the water wash column having a port at a bottom of said water wash column connected to a feed heater and said drain pipe, said feed heater being connected to a feed port at a mid-section of a distillation column, said distillation column including an upper stripping section and a lower stripping section, a heater in a distillation column bottoms, and said transfer tank system connected to said distillation column bottoms, a horizontal condenser connected to said distillation column, a solenoid valve connected to said horizontal condenser and to a second transfer tank system, the second transfer tank system connected to a plurality of drying columns, said plurality of drying columns being connected to final product holding tanks, said final product holding tanks being connected to a third transfer tank system, said third transfer tank system being connected to a plurality of second filters, said plurality of second filters being connected through an optical particle counter, an emergency solvent backup system connected between said third tank transfer system and said plurality of second filters, said waste holding tank being connected to a manifold for recovering vapors and blowdown within said solvent reprocessing system, and a gas chromatograph, a programmed logic controller and computer monitor electrically connected for controlling the solvent reprocessing system.

3. A solvent reprocessing system comprising:
a. an initial waste tank for recovering and storing waste solvent from a blowdown and from a recycle stream;
b. a liquid-to-liquid extraction unit connected for fluid flow to said initial waste tank, including a liquid contact column for contracting a stream of solvent and deionized water, said column including a vertical tube filled with packing material with first and second inlets at different elevations for said deionized water and said solvent, respectively, a top vent, a side overflow and a bottom underflow drain for the exit of said solvent and said water;
c. a distillation column, connected to said extraction unit, including a top condensing section with internal cooling coils, a center section of vertical columns filled with packing material for the efficient contacting of liquid and vapor streams of solvent, and a bottom section containing a heating element for vaporization of the solvent;
d. a drying unit, connected to the distillation column, for drying said solvent through the use of a drying agent, including at least one vertical column with internal screens containing granular drying agent for contacting the liquid solvent with said drying agent, control means for diverting said solvent through said drying unit in a selected sequence, a drying agent regeneration system including inert purge gas flow control, heater and temperature control means for supplying inert purge gas to said drying agent to achieve drying of said granular drying agent;
e. a filtering unit for removing particulate material from the solvent stream, said filtering unit including a plurality of filters in housings arranged in a parallel set of filter trains; and,
f. a final product storage unit, connected to the drying unit, consisting of at least one storage tank with control means for sensing and controlling the flow of solvent into and out of the storage tank.

4. The system of claim 3 for treating of chlorinated solvents.

5. The system of claim 3 for treating of Tricholorethylene (TCE).

6. The system of claim 3 for treating of 1,1,1, Trichloroethane (TCA).

7. The system of claim 3 for treating of Methylene Chloride.

8. The system of claim 3 for treating of Perchloroethylene.

9. The system of claim 3 for treating of Trichlorotrifluoroethane.

10. The system of claim 3 for treating of 1,1,2 Trichlorotrifluoroethane.

11. The system of claim 3 for treating of Alcohol.

12. The system of claim 3 for treating of Methyl Alcohol.

13. The system of claim 3 for treating of Ethyl Alcohol.

14. The system of claim 3 for treating of Isopropyl Alcohol.

15. The system of claim 3 for treating of Butyl Alcohol.

16. The system of claim 3 for treating of Ketones.

17. The system of claim 3 for treating of Methyl Ethylketone (MED).

18. The system of claim 3 for treating of Methyl Isobutylketone (MLKB).

19. The system of claim 3 for treating of Aromatics.

20. The system of claim 3 for treating of n-methyl pyrrolidane.

21. The system of claim 3 for treating of acetone.

* * * * *